United States Patent [19]

Barreras et al.

[11] Patent Number: 4,556,061
[45] Date of Patent: Dec. 3, 1985

[54] CARDIAC PACER WITH BATTERY CONSUMPTION MONITOR CIRCUIT

[75] Inventors: Francisco J. Barreras; Ira R. Baker, both of Miami, Fla.

[73] Assignee: Cordis Corporation, Miami, Fla.

[21] Appl. No.: 710,531

[22] Filed: Mar. 12, 1985

Related U.S. Application Data

[63] Continuation of Ser. No. 409,329, Aug. 18, 1982, abandoned.

[51] Int. Cl.⁴ .............................................. A61N 1/36
[52] U.S. Cl. ............................... 128/419 PT; 320/48; 340/636
[58] Field of Search ................ 128/419 PT, 903–904; 324/426, 429, 433, 436; 320/48; 340/636

[56] References Cited
U.S. PATENT DOCUMENTS

| | | | |
|---|---|---|---|
| 3,742,938 | 7/1973 | Stern | 128/904 |
| 3,832,994 | 9/1974 | Bicher | 128/903 |
| 3,841,336 | 10/1974 | Daynard | 128/419 PT |
| 3,986,498 | 10/1976 | Lewis | 128/904 |
| 4,151,454 | 4/1979 | Lida | 320/48 |
| 4,194,146 | 3/1980 | Patry et al. | 324/433 |
| 4,321,541 | 3/1982 | Nishizuka | 324/426 |
| 4,460,870 | 7/1984 | Finger | 320/48 |

Primary Examiner—William E. Kamm
Assistant Examiner—Mitchell J. Shein
Attorney, Agent, or Firm—Lockwood, Alex, FitzGibbon & Cummings

[57] ABSTRACT

A battery powered implantable cardiac pacer includes a battery consumption monitor circuit which develops within an internal counter a cumulative count of battery consumption in milliampere hours. The consumption count may be read out to an external indicator by a multiplex circuit to provide to the user an indication of battery life remaining. An over-current feature within the monitor circuit provides an alarm signal in the event that battery consumption exceeds a predetermined maximum level.

5 Claims, 5 Drawing Figures

CARDIAC PACER WITH BATTERY CONSUMPTION MONITOR CIRCUIT

This application is a continuation of application Ser. No. 409,329, filed Aug. 8, 1982, now abandoned.

BACKGROUND OF THE INVENTION

The present invention is directed generally to pacemakers, and more particularly to a battery consumption monitoring circuit for use in implantable pacemakers.

Implantable electronic medical devices such as cardiac pacemakers are typically powered by a battery which is implanted with the pacemaker as a single unit. Once the pacemaker has been implanted, the battery is unaccessible and there is no convenient method by which to test its state of depletion. However, because the life of the patient often depends on proper operation of the pacemaker, which in turn is dependent on the condition of the battery, it is imperative that some means of accurately predicting the end of battery life be available to the patient or his physician.

Previous attempts at predicting battery life have centered on periodically subtracting the estimated consumption from the theoretical amp-hour capacity of the battery, and scheduling replacement of the battery as a theoretical limit is reached. This method has not been entirely satisfactory, since the operating parameters of the implanted pacer, and hence the power consumed by the pacer, may vary widely over the life of the pacer, either because of physiological changes in the patient, or because of marked changes in the patient's physical activity. In the past it has been necessary to allow an undesirably wide margin of error in the battery life prediction to guard against these eventualities, thereby forcing premature surgical replacement of the implanted pacer and its battery in many cases, with the attendant risks of complications to the patient.

Other attempts at predicting battery life have involved taking instantaneous current drain measurements by telemetry and from these statistically predicting battery life. However, these measurements do not necessarily remain constant once the patient has left the physician's office, and consequently undesirably large safety factors must still be applied if premature depletion of the battery is to be avoided in all cases.

Various systems are in use for indicating to a patient that the battery of an implanted pacer is nearing depletion, as by varying the output frequency of the pacer, or by providing a marker pulse readable on an ECG. However, such signaling arrangements are only available after-the-fact of impending battery depletion, and may in practice not be immediately noticed by the patient. Furthermore, such warning systems do not give an indication to the user of actual battery life remaining from which he can plan for battery replacement at a convenient time.

The present invention overcomes these problems by providing a continuous indication of the actual quantity of charge consumed from the battery. Since the quantity of charge available from a given battery can be accurately calculated, the remaining battery life can be readily determined with accuracy.

SUMMARY OF THE INVENTION

A battery consumption monitor system, for use in an implantable cardiac pacer, or like utilization means, includes current sensing means coupled between the battery and the pacer or other utilization means for developing a demand signal indicative of current drain from the battery. Means including a counter responsive to the demand signal produce an output signal dependent on the cumulative current drawn from the battery, and output circuit means produce an output signal indicative of the counting state of the counter.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several Figures of which like reference numerals identify like elements, and in which:

DESCRIPTION OF THE PREFERRED EMBODIMENT

Figure 1:
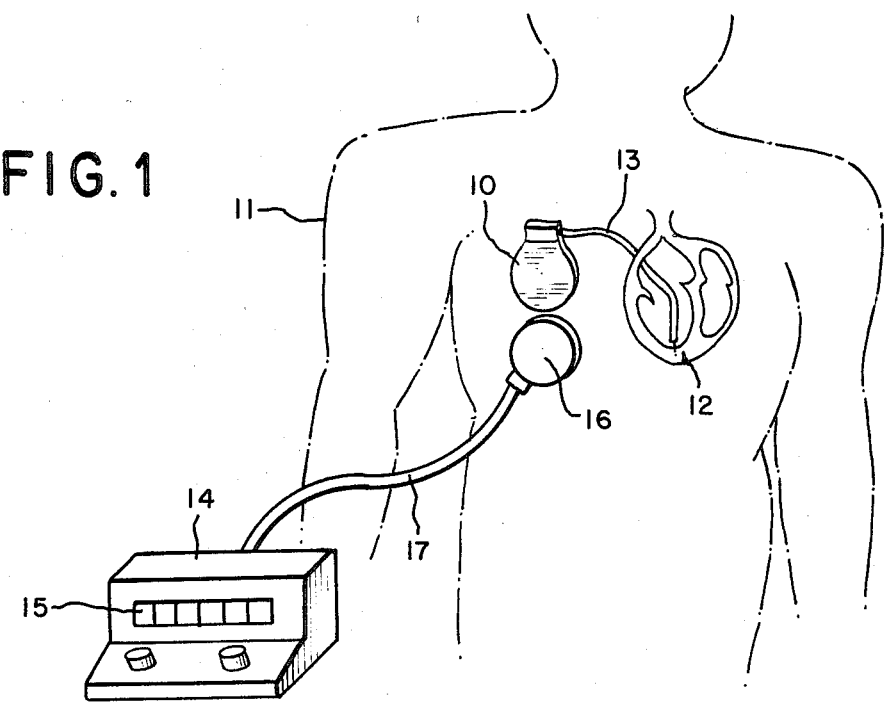
FIG. 1 is a perspective view of a battery powered implantable cardiac pacer including a battery consumption monitoring system constructed in accordance with the invention.

Referring to the Figures, and particularly to FIG. 1, a battery-operated implantable cardiac pacer 10 is shown implanted within a patient 11. The output of the pacer is connected to the patient's heart 12 (shown in cross section) by means of a pacer lead 13, which may be conventional in construction and operation. The pacer 10 is preferably formed as a unitary self-contained sealed device such that its operation is unaffected by exposure to body fluids.

Operation of the pacer can be monitored by multiplextype monitor apparatus 14 external to the body and viewable by the patient or the attending physician. The monitoring apparatus 14 includes a digital readout 15 on which, in accordance with the invention, an indication of consumed battery capacity is provided. Communication between apparatus 14 and pacer 10 may be provided by a magnetic or radio-frequency pickup 16 positioned by the user on the chest of the patient in close proximity to the pacer. The pickup receives telemetry data from the pacer in a manner well known to the art, and the resulting electrical signal is conveyed to apparatus 14 through a flexible electrical cable 17.

In use, the life remaining in the battery contained within the implanted pacer 10 can be determined at any time by positioning pickup 16 in communication with the pacer. Interrogation signals are then applied to the pacer, wherein conventional telemetering circuitry responds by providing an output indicative of the charge actually consumed by the pacer circuitry from the battery up to that point. Knowing this information, and the available current capacity of the battery, the user can readily determine the actual battery life remaining.

Figure 2:
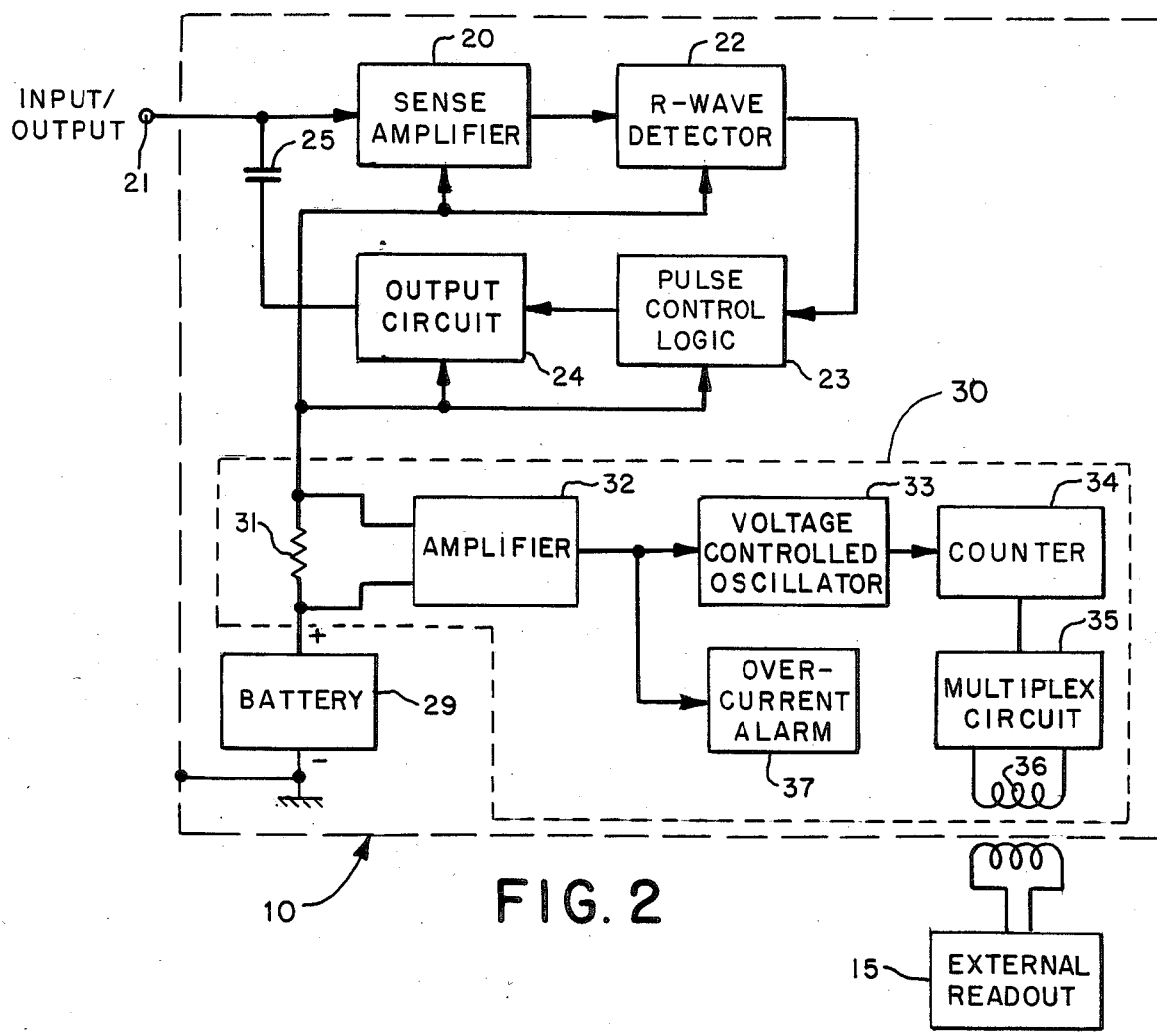
FIG. 2 is a functional block diagram showing the principal elements of the cardiac pacer of FIG. 1.

Referring to FIG. 2, the implanted cardiac pacer 10 is seen to include in accordance with conventional practice a sense amplifier 20 which amplifies the R-wave conveyed to the pacer by pacer lead 13 and connector 21. Preferably, amplifier 20 has a bandpass characteristic which attenuates noise and other extraneous signals picked-up by the pacer lead, so that the detected R-wave may be more effectively amplified. The amplified sense signal is applied to an R-wave detector 22, which provides an output pulse upon the occurrence of an R-wave component in the sensed signal.

The detector output pulse is applied to a pulse control logic circuit 23, which under appropriate circumstances produces an output control pulse. This control pulse is applied to an output circuit 24 wherein it causes the generation of a pacer output pulse of predetermined amplitude and duration. This output pulse is applied through an output capacitor 25 to pacer lead 13, which conveys the pulse to the heart. In practice, pulse control logic circuit 23 causes output circuit 24 to produce a pacer output pulse only in the event that an R-wave resulting from natural heart activity is not detected within a selected time period.

Operating power for the implanted pacer 10 is obtained from a self-contained battery 29, which may be a conventional type intended for use in implanted pacemakers, such as the lithium type now widely used in such applications. The negative polarity output terminal of battery 29 is connected to pacer ground, and in accordance with conventional practice is connected to an electrically conductive outer surface on the pacer to establish a ground reference for the pacer output pulses. The positive-polarity battery terminal is connected to the various circuits of the pacer and serves to supply unidirectional operating current for their operation.

To provide an indication of consumed battery capacity, the unidirectional current developed by battery 29 is applied to the pacer circuitry through a battery consumption monitor circuit 30 which includes a series-connected current-metering resistor 31. A voltage is produced across this resistor which is proportional to the current demand of the pacer circuitry. This voltage is applied to an amplifier 32. The amplified current-indicative signal at the output of amplifier 32 is applied to a voltage controlled oscillator 33 which produces an output signal having a frequency dependent on the applied voltage level, and hence on the current demand of the pacer circuitry. This signal is applied to a counter 34, wherein a cumulative count is developed which is representative of the total energy consumed from the battery. This count may be read out by means of conventional telemetry circuitry 35 which functions in conjunction with a pickup coil 36 in a manner well known to the art to convey the count in the counter to external apparatus, such as the previously described display apparatus. The multiplex circuit 35 may also serve to vary the operating parameters of the pacer in response to command signals from external control apparatus, thus performing the dual functions of reading out parameters of the pacer for display to an operator, and of conveying commands from the operator to change the operating parameters of the pacer.

An additional feature of the battery consumption monitor system is the provision of an over-current alarm 37 which provides an alarm in the event that the current through sensing register 31 exceeds a predetermined maximum level. To this end, over-current alarm 37 continuously compares the amplified sensing signal from the amplifier 32 against an internally provided reference corresponding to the current limit, and in the event of a comparison provides the alarm output signal. The alarm may take the form of a variation in pacing rate, in which case the alarm output is connected to pulse control logic circuit 23. Alternatively, the over-current alarm may take the form of an implanted device which vibrates to alert the patient. In either event, the patient is alerted to the over-current condition, and the probable malfunction of the pacer circuitry.

Figure 3:
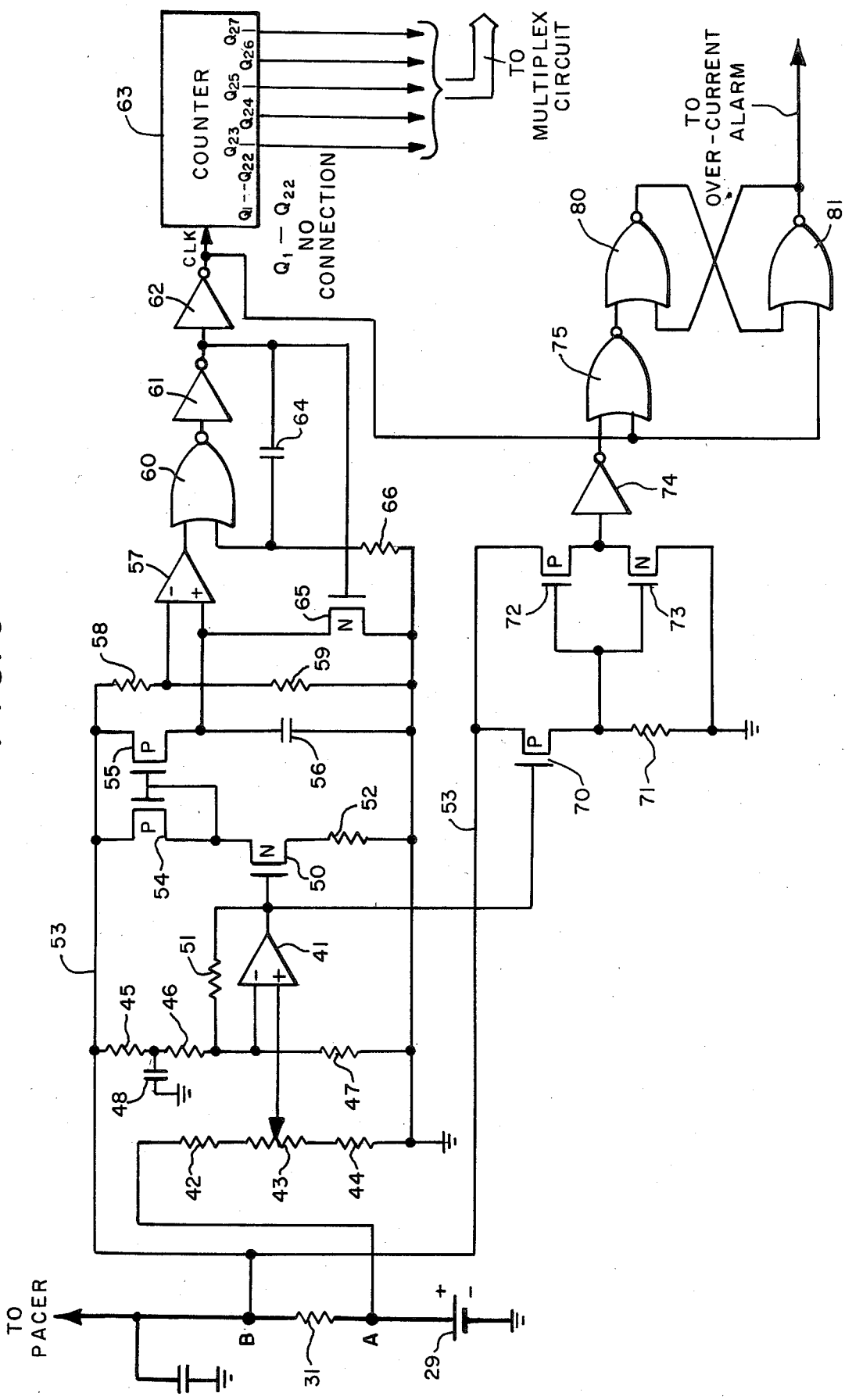
FIG. 3 is a simplified schematic diagram of the battery consumption monitor system.

Referring to FIG. 3, the battery consumption monitor circuit 30 is seen to comprise a differential amplifier 41 for comparing the voltage levels on either side of the current sensing resistor 31. The voltage level on the upline or battery side (at point A) of resistor 31 is applied ro the non-inverting input of the comparator through a voltage divider network comprising a resistor 42, a potentiometer 43, and a resistor 44. Depending on the position of the arm of potentiometer 43, a predetermined portion of the terminal A voltage is impressed on the non-inverting input.

A predetermined portion of the downline voltage at resistor 31, (at point B) is applied to the inverting input through a second voltage divider comprising resistors 45, 46 and 47. The juncture of resistors 45 and 46 is connected to ground through a capacitor 48 to provide filtering at the comparator input, and the inverting input of the comparator is connected to the juncture of resistors 46 and 47. The output of comparator 41 is applied to the base electrode of an N-type transistor 50 and by a resistor 51 to the juncture of resistors 46 and 47. With this arrangement, an amplified output signal is developed at the output of comparator 41 having a voltage level dependent on the current drawn by the pacer from battery 29 through resistor 31.

The variable voltage signal from comparator 41 is converted to a variable current signal by N-type transistor 50, which has one principal electrode oonnected to ground through a resistor 52 and its other principal electrode connected to the supply line 53 through the principal electrodes of a P-type transistor 54. The current through the principal electrodes of transistor 50 is proportional to the voltage level at the output of comparator 41, and hence to the current through sensing resistor 31. This current is mirrored by a pair of P-type transistors 54 and 55 connected back-to-back, with the principal electrode of transistor 50 being connected to the two control electrodes of the transistor pair.

The principal electrodes of transistor 55 are connected to supply line 53, and through a capacitor 56 to ground. The juncture of capacitor 56 and transistor 55 is connected to the non-inverting input of a second comparator amplifier 57. The inverting terminal of comparator 57 has a predetermined reference voltage applied to it by a voltage divider comprising a pair of resistors 58 and 59 connected between supply line 53 and ground. The output of comparator 57 is applied through a NOR gate 60 and a pair of inverters 61 and 62 to the clock input of a 27-bit ripple counter 63. The output of inverter 61 is also connected to the base electrode of a transistor 65 having principal electrodes connected across timing capacitor 56. The remaining input of NOR gate 60 is connected by a capacitor 64 to inverter 61 and by a resistor 66 to ground.

In operation, capacitor 56 is charged from supply line 53 through transistor 55. Since the current level at transistor 55 is a function of the voltage output at comparator 41, and hence the current drawn through sensing resistor 31, the time required to charge capacitor 56 to a selected reference level is dependent on the current required by the pacer. The greater the required current, the more quickly capacitor 56 is charged.

The reference level to which capacitor 56 is charged is set by the voltage applied by resistors 58 and 59 to the inverting input of comparator 57. When this reference level is reached, an output is produced by comparator 57 which is applied through NOR gate 60 and inverter 61 to the control electrode of transistor 65. This conditions the transistor into saturation, causing capacitor 56 to be discharged. After capacitor 56 has discharged, an output is no longer produced by comparator 57. To prevent the capacitor 56 from immediately recharging capacitor 64 and resistor 66 provide a continuing signal for a short interval on OR gate 60. This causes an output pulse of predetermined fixed duration to be produced.

As a result of the continued charging and discharging of capacitor 56, a series of pulses are produced at the output of inverter 62 at a frequency dependent on the current through sensing resistor 31. Comparator amplifier 41 and its associated circuitry functions as a linear amplifier, and transistor 50, timing capacitor 56, comparator 57 and their associated circuitry functions as a voltage-controlled oscillator.

The pulses produced at the output of inverter 62 are applied to counter 63, causing that device to count upwards one count for each applied pulse. In practice, the gain of amplifier 41 and its related circuits is such that counter 63 is advanced once for each milliampere hour drawn from the battery. As a result, at any given instant the count contained in counter 63 is equal to the number of milliampere-hours consumed from the battery.

Although the entire count in counter 63 may be read out through the multiplex circuit 35 (FIG. 2) of the pacer, in practice it is only necessary to read out the five most significant digits. The multiplex circuitry required for this purpose may be entirely conventional in construction and operation.

The additional function of monitoring for excessive current drain is accomplished by applying the amplified variable-voltage signal developed by comparator amplifier 41 to the base electrode of a P-type transistor 70. One principal electrode of this transistor is connected to supply line 53, and the other principal electrode is connected to ground through a resistor 71. The signal developed across resistor 71 is applied to the base electrodes of a pair of P and N-type transistors 72 and 73 having principal electrodes connected in series between supply line 53 and ground. The juncture of these transistors is connected through an inverter 74 to one input of a NOR gate 75. The other input of NOR gate 75 is connected to the output of inverter 62.

In operation, the amplified current-indicative variable-voltage signal from comparator 41 causes transistor 70 to develop a current-indicative signal across resistor 71. This signal is applied to transistors 72 and 73, where it causes these devices to conduct when the current falls above the established threshold, and to cut-off when the current level falls below the threshold. The resulting alarm signal, developed at the juncture of the two transistors, is applied through inverter 74 to NOR gate 75.

The output of NOR gate 75 is applied to one input of a NOR gate 80. The output of NOR gate 80 is applied to one input of a NOR gate 81. The output of NOR gate 81 is applied to the remaining input of NOR gate 80. The output of inverter 62 is applied to the remaining input of inverter 81.

NOR gates 80 and 81 operate in a manner well known to the art to form a latch circuit which latches in the presence of an applied alarm signal from inverter 74. The latched alarm signal, present at the output of NOR gate 81, is applied to an appropriate failure alarm such as a rate modification circuit in pulse control logic circuit 23 (FIG. 2), or a mechanical alarm device of conventional construction (not shown). In the event of an over-current condition the appropriate alarm device is actuated to alert the patient to a malfunction in the pacer, enabling corrective action to be taken to preclude premature battery failure.

Figure 4:
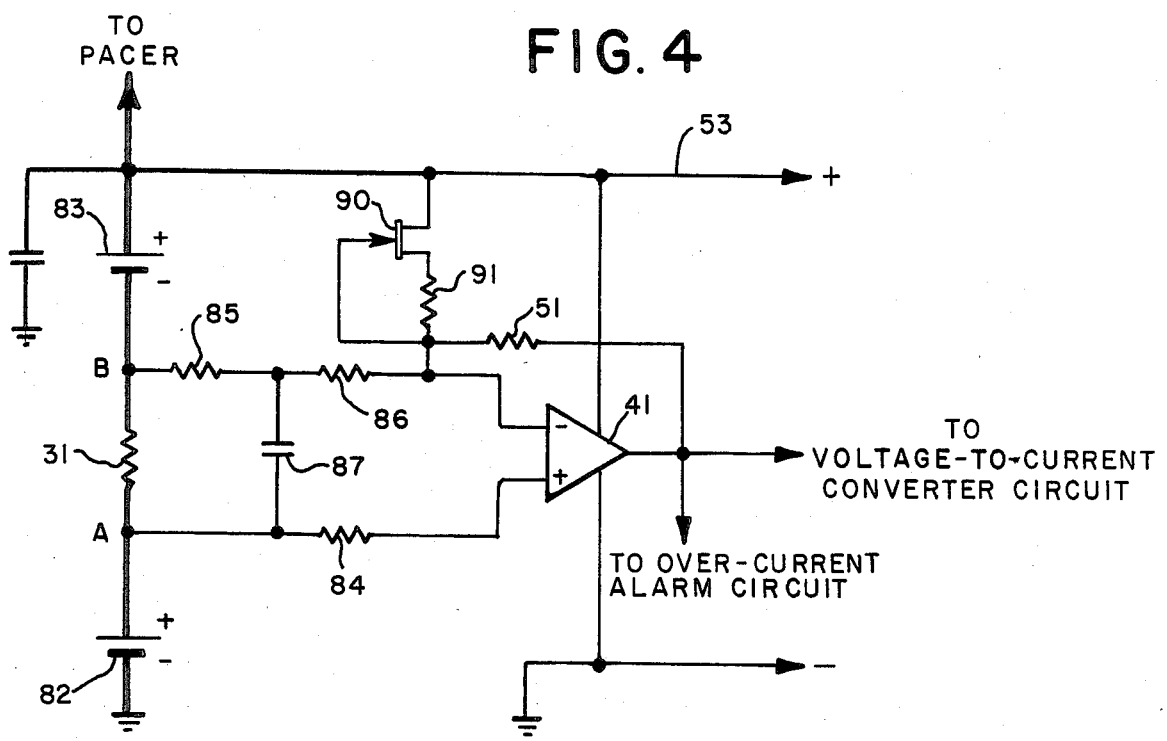
FIG. 4 is a simplified schematic diagram of a portion of the battery usage monitoring system showing an alternative current sensing circuit for use in conjunction with series-connected batteries.

Referring to FIG. 4, the battery consumption monitor circuit of the invention may be utilized in conjunction with a pacer powered by two batteries. In this case, the sensing resistor 31 is located between two serially-connected batteries 82 and 83. The batteries are selected to provide when connected in series the required operating voltage of the pacer. The upline (A) connection of resistor 31 is applied through a resistor 84 to the non-inverting input of comparator amplifier 41. The downline (B) connection of resistor 31 is applied through a filter network comprising the series combination of resistors 85 and 86 to the inverting input of comparator amplifier 41. A filter capacitor 87 is connected between the juncture of the resistors 85 and 86 and resistor 81. The operating point of comparator amplifier 41 is set by a unijunction transistor 90 connected in series with a resistor 91 between the inverting input of the comparator and the supply line 53 of the pacer.

In operation, the voltage developed across sensing resistor 31 is applied to the terminals of comparator amplifier 41 to produce at the output of the comparator an amplified signal having a voltage level dependent on pacer current drain. As in the single battery embodiment, a change in current drain causes a proportional change in the charging current of capacitor 56 and consequently, a proportional change in the repetition rate, or frequency, at the output of inverter 62. Therefore, counter 63 is caused to accumulate a count representative of the cumulative current drain from the batteries. In all other respects, the monitor circuit may be identical to that shown in FIG. 3.

Figure 5:
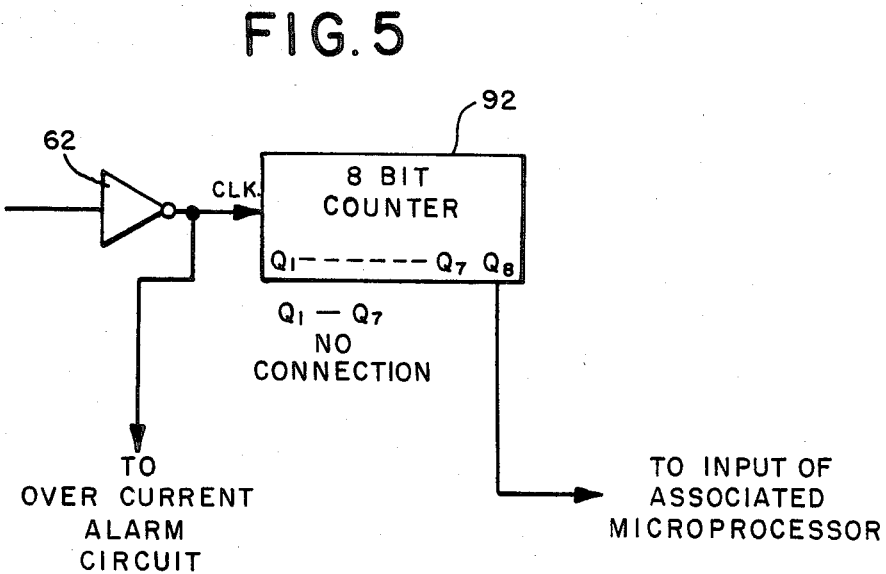
FIG. 5 is a simplified schematic diagram of a portion of the battery consumption monitoring system showing an alternative output circuit for use in conjunction with an external microprocessor.

Referring to FIG. 5, the size of the 27-bit ripple counter 63 may be reduced by utilizing external storage and counting capability, such as may be found in an external microprocessor. To this end, the output of inverter 62 may be alternatively applied to an eight-bit ripple counter 92 arranged to accumulate the pulses produced by the voltage controlled oscillator formed by transistors 50, 54, 55, comparator 57, NOR gate 60 and inverters 61 and 62. In this case, only the most significant ($Q_8$) output of the counter is connected to the multiplex circuit, since the external counting capability requires only the overflow from the counter.

The gain of comparator amplifier 41 and the associated circuitry of the voltage controlled oscillator may be advantageously selected to enter a count into counter 63 (FIG. 3) following each 1 milliampere hour consumed from the battery. Assuming a typical current drain of 20.7 microamperes for the cardiac pacer, and a 2.0 ampere house battery capacity, a theoretical battery life of 11 years is indicated. For the average current drain, the voltage controlled oscillator will operate at a frequency of 0.5 hertz, or 1 pulse every 2 seconds. Since there are 31,536,000 seconds in one year, it follows that 15,768,000 clock pulses will be counted by the counter each

| YEAR | TOTAL COUNT | BCD READING AMP/HOURS | FIVE MOST SIGNIFICANT BITS | | | | |
|---|---|---|---|---|---|---|---|
| | | | 1 | 2 | 3 | 4 | 5 |
| 1 | 15,768,000 | 0.1 | 1 | 0 | 0 | 0 | 0 |
| 2 | 31,536,000 | 0.3 | 1 | 1 | 0 | 0 | 0 |
| 3 | 47,304,000 | 0.5 | 1 | 0 | 1 | 0 | 0 |
| 4 | 63,072,000 | 0.7 | 1 | 1 | 1 | 0 | 0 |
| 5 | 78,840,000 | 0.9 | 1 | 0 | 0 | 1 | 0 |
| 6 | 94,608,000 | 1.1 | 1 | 1 | 0 | 1 | 0 |
| 7 | 110,376,000 | 1.3 | 1 | 0 | 1 | 1 | 0 |
| 8 | 126,144,000 | 1.5 | 1 | 1 | 1 | 1 | 0 |
| 9 | 141,912,000 | 1.6 | 0 | 0 | 0 | 0 | 1 |
| 10 | 157,680,000 | 1.8 | 0 | 1 | 0 | 0 | 1 |
| 11 | 173,448,000 | 2.0 | 0 | 0 | 1 | 0 | 1 |

From the above, it is seen that by reading out the counting state of counter 63 on a regular basis it is possible to accurately determine the actual energy consumed from the battery, and hence the energy remaining for consumption. Alternatively, the counter may be initially set to the theoretical maximum energy capacity of the battery, and then counted down with each increment of energy consumption to read out directly battery consumption remaining.

While the battery consumption monitoring circuit has been shown in conjunction with an implanted cardiac pacer, it will be appreciated that the circuit can be utilized with other types of devices intended to operate from a battery over a long time period, such as implantable pumps, telemetering devices, instrumentation, and the like.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A battery-operated implantable pacer comprising, in combination:
    pacer circuit means operable from a unidirectional current source for supplying pacing pulses to a pacer lead;
    means including a battery for supplying unidirectional current to said pacer circuit means;
    current sensing means coupled between said battery and said pacer circuit means for developing a demand signal indicative of the current being drawn from said battery;
    oscillator means responsive to said demand signal for developing a plurality of pulses each indicative of the consumption of a predetermined unit of charge by said pacer circuit means from said battery;
    counter means responsive to said pulses for developing a multi-digit output signal continuously indicative of the number of units of charge consumed from said battery, said counter means including a plurality of individual counter elements providing respective digits of said output signal; and
    telemetry circuit means responsive to said output signal for providing at a remote location within said range of battery charge states an indication of the total charge consumed from said battery.

2. A battery-operated implantable pacer as defined in claim 1 wherein said current sensing means comprise a resistor connected in series between said battery and said pacer circuit.

3. A battery-operated implantable pacer as defined in claim 2 wherein said oscillator means comprise a voltage controlled oscillator responsive to the voltage developed across said resistor for developing said pulses at a rate proportional to said voltage.

4. A battery-operated pacer as defined in claim 1 wherein said individual counter elements provide only a predetermined most-significant portion of the total count capacity of said counter.

5. A battery-operated implantable pacer as defined in claim 1 including an over-current alarm responsive to said demand signal for providing an alarm to the patient upon the current drawn from said battery exceeding a predetermined maximum level.

* * * * *